(12) United States Patent
Allegrini et al.

(10) Patent No.: US 8,097,724 B2
(45) Date of Patent: Jan. 17, 2012

(54) PROCESS FOR THE PREPARATION OF SITAGLIPTIN

(75) Inventors: Pietro Allegrini, San Donato Milanese (IT); Emanuele Attolino, Palagiano (IT); Gianmaria Dell'Anna, Milan (IT); Mario Michieletti, Novara (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 12/727,566

(22) Filed: Mar. 19, 2010

(65) Prior Publication Data

US 2010/0331541 A1    Dec. 30, 2010

(30) Foreign Application Priority Data

Jun. 30, 2009   (IT) .............................. MI2009A1149

(51) Int. Cl.
*C07D 491/00* (2006.01)
(52) U.S. Cl. ..................................................... 544/350
(58) Field of Classification Search .................... 544/350
See application file for complete search history.

(56) References Cited

U.S. PATENT DOCUMENTS 6,699,871 B2   3/2004   Edmondson

FOREIGN PATENT DOCUMENTS

WO    2005097733 A1    10/2005
WO    2006081151 A1    8/2006

*Primary Examiner* — James O Wilson
*Assistant Examiner* — Douglas M Wills
(74) *Attorney, Agent, or Firm* — Rothwell, Figg, Ernst & Manbeck, P.C.

(57) ABSTRACT

A process for the preparation of a compound of formula (I) such as 2(R)-4-oxo-4-[3-(trifluoromethyl)-5,6-dihydro[1,2,4]triazolo[4,3-a]-7(8H)-pyrazinyl]-1-(2,4,5-trifluorophenyl)-2-butanamine, or a salt thereof, in the anhydrous or hydrated form, either as a mixture of enantiomers, or as a single (R) or (S) enantiomer,

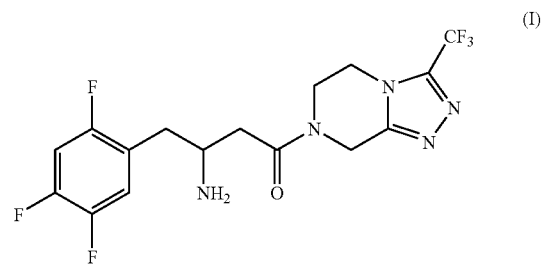

(I)

comprising the conversion of a compound of formula (II), or a salt thereof, either as a single (R) or (S) enantiomer or as a mixture thereof

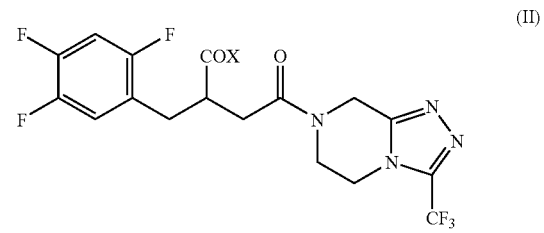

(II)

wherein X is hydrogen, hydroxy, C1-C8 alkyl, C1-C4 alkoxy, aryl, amino, N3 or halogen; into a compound of formula (I), and if desired, the separation of a single enantiomer of formula (I) from the racemic mixture, and/or, if desired, the conversion of a compound of formula (I) into a salt thereof, or vice versa.

16 Claims, No Drawings

PROCESS FOR THE PREPARATION OF SITAGLIPTIN

FIELD OF THE INVENTION

The present invention relates to a novel process for the preparation of 2(R)-4-oxo-4-[3-(trifluoromethyl)-5,6-dihydro[1,2,4]triazolo[4,3-a]-7(8H)-pyrazinyl]-1-(2,4,5-trifluorophenyl)-2-butanamine and intermediates useful in its synthesis.

TECHNOLOGICAL BACKGROUND

2(R)-4-Oxo-4-[3-(trifluoromethyl)-5,6-dihydro[1,2,4]triazolo[4,3-a]-7(8H)-pyrazinyl]-1-(2,4,5-trifluorophenyl)-2-butanamine, namely Sitagliptin, having the following formula

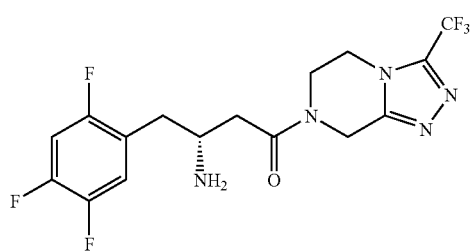

is used in the form of the phosphate monohydrate salt in the treatment of diabetes mellitus of Type II U.S. Pat. No. 6,699,871 discloses the synthesis of Sitagliptin according to the scheme reported below. In particular, the protected β-amino acid of formula (A) is coupled with an amine of formula (B) in the presence of a carbodiimide (EDC), hydroxybenzotriazole (HOBT), diisopropylethylamine (DIPEA) and dimethylformamide (DMF) to obtain a compound of formula (C) which is converted to Sitagliptin by deprotection of the amine function.

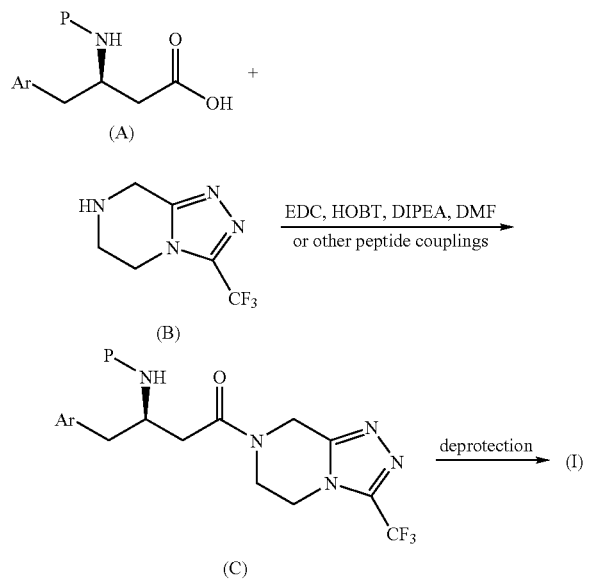

U.S. Pat. No. 6,699,871 also discloses the preparation of the β-amino acid compound (A) and of the amine (B) hydrochloride. In particular, the preparation of the β-amino acid compound (A) is carried out starting from corresponding α-amino acid by Arndt-Eistert homologation reaction with diazomethane, a toxic and explosive reagent. Said process is hardly applicable on an industrial scale due to the high cost of the intermediates used and the safety problems the use of diazomethane involves.

WO 2005/097733 and WO 2006/081151 disclose the preparation of Sitagliptin by stereoselective catalytic hydrogenation of a β-amino acrylamide. This kind of process is also affected with important problems concerning industrial applicability, due to the high cost of intermediates such as 2,4,5-trifluorophenylacetic acid and 2,2-dimethyl-1,3-dioxane-4,6-dione (Meldrum's acid). Furthermore, the stereoselective catalytic hydrogenation of the β-amino acrylamide is carried out using sophisticated and fragile Rh(I) complexes in the presence of expensive diphosphine ligands, which prevent their applicability on an industrial scale.

As can be appreciated these processes involve the use of either toxic, dangerous reagents such as diazomethane, or difficult and costly to prepare starting materials or complex catalytic systems which consequently remarkably affect costs. There is therefore the need for an alternative synthetic route which provides Sitagliptin or a salt thereof, having high enantiomeric and chemical purity, starting from low cost starting materials.

SUMMARY OF THE INVENTION

A process has now been found which allows to obtain Sitagliptin from low cost starting materials and with safe, reproducible procedures. Therefore, when carried out on industrial scale the process of the present invention is advantageous over those presently used.

DETAILED DISCLOSURE OF THE INVENTION

The object of the invention is a process for the preparation of a compound of formula (I) or a salt thereof, in the anhydrous or hydrated form, as a mixture of enantiomers, or as a single (R) or (S) enantiomer,

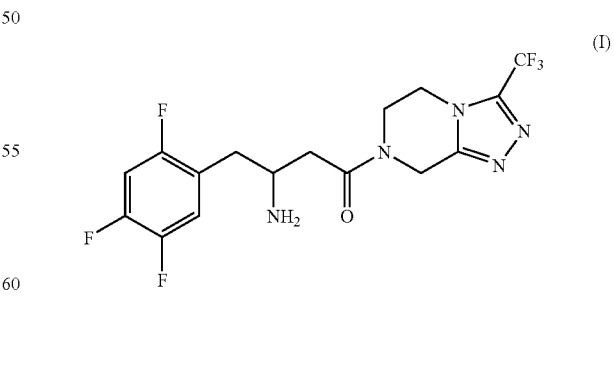

comprising the conversion of a compound (II) or a salt thereof, as a single (R) or (S) enantiomer or as a mixture thereof

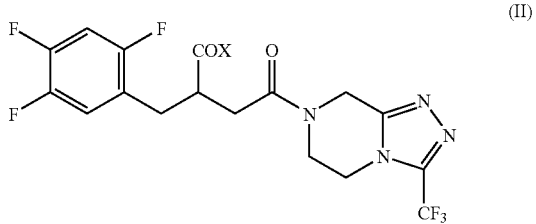

(II)

wherein X is hydrogen, hydroxy, $C_1$-$C_8$ alkyl, $C_1$-$C_4$ alkoxy, aryl, amino, $N_3$ or halogen; to a compound of formula (I), and if desired, the separation of a single enantiomer of formula (I) from the racemic mixture, and/or, if desired, the conversion of a compound (I) to a salt thereof, or vice versa.

An enantiomer of a compound (I) or (II) is preferably in absolute configuration (R).

A $C_1$-$C_8$ alkyl group, which can be a straight or branched group, is for example a $C_1$-$C_6$ alkyl group, preferably a $C_1$-$C_4$ alkyl group, in particular methyl, ethyl or isopropyl.

A $C_1$-$C_4$ alkoxy group, which can be straight or branched, is for example methoxy, ethoxy or isopropoxy.

An aryl group is for example phenyl or naphthyl, preferably phenyl.

A halogen group is for example chlorine or bromine.

A salt of a compound of formula (I) or (II) is typically a pharmaceutically acceptable salt thereof, for example the salt of a compound of formula (I) is the phosphate salt, in the anhydrous or hydrated form, preferably in the monohydrate form.

A compound of formula (II), or a salt thereof, as a single enantiomer or as a mixture thereof, is a novel compound and is a further object of the present invention. The compounds of formula (II) in which X is hydroxy are preferred.

According to a preferred feature of the invention, a compound of formula (I), or a salt thereof, as a single enantiomer or as a mixture thereof, can be obtained for example by a process comprising the conversion of a compound of formula (II), as defined above in which X is $N_3$, either as a single enantiomer or as a mixture thereof, via Curtius rearrangement, to obtain an intermediate isocyanate of formula (III), as a single enantiomer or as a mixture thereof;

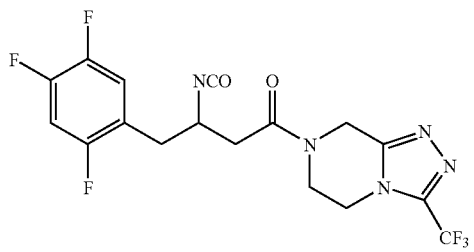

(III)

its subsequent hydrolysis to afford the compound of formula (I), and, if desired, the separation of a single enantiomer of formula (I) from the racemic mixture, and/or, if desired, the conversion of a compound of formula (I) to a salt thereof, or vice versa.

The Curtius rearrangement reaction can be carried out in a solvent, selected from for example from the group comprising a dipolar aprotic solvent, typically dimethylformamide, dimethylacetamide, acetonitrile or dimethylsulfoxide; a cyclic or acyclic ether, typically tetrahydrofuran, dioxane or methyl-tert-butyl ether; a chlorinated solvent, typically dichloromethane; an apolar solvent, typically toluene; an ester, typically ethyl acetate, isopropyl acetate or butyl acetate; and a ketone, typically acetone, methyl ethyl ketone or methyl isobutyl ketone; or a mixture of two or more, preferably two or three, of said solvents.

After completion of the rearrangement, a compound of formula (III) can be isolated or not.

According to a preferred feature of the invention, the same Curtius reaction can alternatively be carried out in one of the solvents or a mixture thereof, as defined above, preferably in toluene, in the presence of water at neutral or acid pH.

The intermediate isocyanate (III) can be hydrolysed to obtain the compound of formula (I), for example, by treatment with water according to known methods. The hydrolysis reaction is preferably carried out at neutral or acid pH.

According to a further preferred feature of the invention, a compound of formula (I), or a salt thereof, as a single enantiomer or as a mixture thereof, can for example be obtained by a process comprising the conversion of a compound of formula (II), as defined above in which X is $N_3$, either as a single enantiomer or as a mixture thereof, via Curtius rearrangement in the presence of an alcohol, preferably of a $C_1$-$C_4$ alkanol, or of a thiol containing $C_2$-$C_{20}$ carbon atoms, for example a $C_2$-$C_{20}$ alkyl-thiol, aryl-thiol, or aryl-$C_1$-$C_4$-alkyl-thiol, to obtain a compound of formula (IV) in racemic form or in an optically active (R) or (S) form

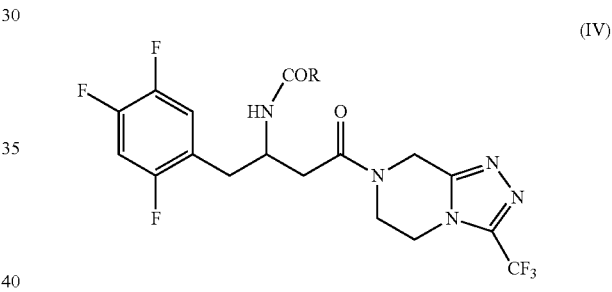

(IV)

wherein R is a $C_1$-$C_4$ alkoxy group, or for example $C_2$-$C_{20}$ alkylthio, arylthio, or aryl-$C_1$-$C_4$ alkylthio; its subsequent hydrolysis to give a compound of formula (I), and if desired, the separation of a single enantiomer of formula (I) from the racemic mixture, and/or if desired, the conversion of a compound of formula (I) to a salt thereof, or vice versa.

A $C_1$-$C_4$ alkanol, which can be straight or branched, is preferably isopropanol or tert-butanol.

A $C_2$-$C_{20}$ alkyl-thiol, which can be straight or branched, is for example dodecanethiol.

The aryl residue in an arylthio or aryl-$C_1$-$C_4$ alkylthio group can be phenyl or naphthyl, or an unsaturated heteromonocycle or heterobicycle, containing 1 to 3 heteroatoms independently selected from oxygen, sulfur and nitrogen. An aryl-thiol is preferably thiophenol or mercaptobenzimidazole. A thiol, as exemplified above, is more preferably dodecanethiol.

The Curtius rearrangement can be carried out in one or more solvents, preferably 1, 2 or 3, selected from those indicated above, preferably tetrahydrofuran.

After completion of the rearrangement a compound of formula (IV) can be isolated or not.

The hydrolysis of a compound of formula (IV) can be carried out by saponification using an aqueous solution of a base if the case in the presence of a water-miscible or immiscible organic cosolvent.

A base can be for example a carbonate, hydroxide or phosphate of an alkali metal, preferably sodium or potassium.

An organic cosolvent is for example a solvent selected from the group comprising a dipolar aprotic solvent, typically dimethylformamide, dimethylacetamide, acetonitrile or dimethylsulfoxide; a cyclic or acyclic ether, typically tetrahydrofuran, dioxane or methyl-tert-butyl ether; a chlorinated solvent, typically dichloromethane; an apolar solvent, typically toluene; a polar protic solvent, preferably a $C_1$-$C_4$ alkanol; and a ketone, typically acetone, methyl ethyl ketone or methyl isobutyl ketone; or a mixture of two or more, preferably two or three, of said solvents.

Both the Curtius rearrangement and the hydrolysis reactions described above can be carried out at temperatures approximately ranging from 20° C. to the reflux temperature of the solvent.

According to a further preferred aspect of the invention, a compound of formula (I), or a salt thereof, as a single enantiomer or as a mixture thereof, can be obtained from a compound of formula (II) as defined above, wherein X is hydroxy, by its conversion into a compound of formula (II), in which X is $N_3$, by treatment with diphenylphosphoryl azide (DPPA), and subsequent Curtius rearrangement according to the procedures reported above. Said conversion can be carried out in two separated steps or in a single step (one-pot reaction).

According to a further preferred aspect of the invention, a compound of formula (I), or a salt thereof, as a single enantiomer or as a mixture thereof, can be obtained from a compound of formula (II) as defined above, wherein X is hydroxy, via conversion to a compound of formula (III) as defined above, prepared according to the known Lossen or Schmidt rearrangement procedures and subsequent hydrolysis according to what reported above.

According to a further preferred aspect of the invention, a compound of formula (I), or a salt thereof, as a single enantiomer or as a mixture thereof, can be obtained by Hofmann degradation reaction of a compound of formula (II), as defined above in which X is $NH_2$, as a single enantiomer or as a mixture thereof and, if desired, the separation of a single enantiomer of formula (I) from the racemic mixture, and/or if desired, the conversion of a compound of formula (I) to a salt thereof, or vice versa.

The reaction can be carried out by treatment with a reagent capable of providing halogen ions in oxidation state (I), preferably hypobromite or hypochlorite ions.

Said reagent is for example a hypochlorite or hypobromite salt with a cation of an alkali metal, preferably sodium or potassium, or with an organic cation, such as an alkylammonium, e.g. tetrabutylammonium. The hypochlorite and the hypobromite can be prepared by dissolving molecular chlorine or bromine in a suitable basic aqueous solution, or using reagents able to develop molecular chlorine or bromine in situ, in an alkali medium, e.g. N-bromosuccinimide.

If desired, the Hofmann reaction can be carried out using a hypobromite or hypochlorite aqueous solution, as defined above, which has been made basic by the presence of a hydroxide of an alkali metal, for example sodium or potassium.

If desired, the Hofmann reaction can be carried out using an alcoholic basic solution, which is basic for example by the presence of a tertiary amine or an alkali metal $C_1$-$C_4$ alkoxide, and isolating the intermediate carbamate of formula (IV), as defined above wherein R is a $C_1$-$C_4$ alkoxy group, which by basic hydrolysis affords a compound of formula (I) in the optically active form as a single enantiomer or a mixture thereof.

A $C_1$-$C_4$ alkoxide of an alkali metal is preferably a sodium or potassium salt, for example sodium or potassium methoxide or ethoxide.

A tertiary amine can be for example 1,8-diazabicyclo[5.4.0]undec-7-ene (DBU), 1,5-diazabicyclo[4.3.0]non-5-ene (DBN), or 1,4-diazabicyclo[2.2.2]octane (DABCO).

The separation of a single enantiomer of a compound of formula (I), or a salt thereof, for example the single isomer in the optically active (R) or (S) form, from an enantiomeric mixture can be carried out according to known methods, for example by resolution using an optically active acid.

The conversion of a compound of formula (I) to a salt thereof, or the conversion of a salt thereof to the free base, can be obtained according to known methods.

A resulting compound of formula (I), in particular with absolute configuration (R), i.e. Sitagliptin, has purity equal to or higher than 99%, in particular equal to or higher than 99.9%.

Sitagliptin with such a purity degree can be used for the preparation of a salt thereof, for example the phosphate monohydrate, having the same purity degree.

The enantiomeric purity of Sitagliptin, obtained according to the invention, is equal to or higher than 99.0%. Said purity can be optionally increased up to e.g. 99.9% by means of known techniques, for example by crystallization.

The size of the Sitagliptin crystals, as obtainable according to present invention, is characterized by a $D_{50}$ value approximately ranging from 10 to 250 µm. If desired, said value can be reduced by micronisation or fine grinding.

A compound of formula (II), as defined above, in which X is hydroxy, or a salt thereof, can be prepared for example by hydrolysis and decarboxylation of a compound of formula (V)

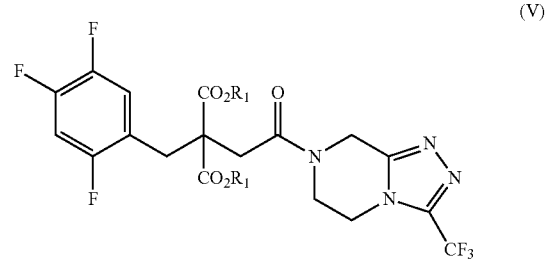

wherein each $R_1$, which can be the same or different, is straight or branched $C_1$-$C_4$ alkyl, and if desired, the conversion to a salt thereof or vice versa.

The $R_1$ groups are preferably the same and are methyl or ethyl.

The hydrolysis and the subsequent decarboxylation of a compound of formula (V) can be carried out for example by treating a solution thereof in a $C_1$-$C_4$ alkanol, for example methanol or ethanol, with an alkali metal hydroxide aqueous solution, preferably sodium or potassium, and readjusting the resulting mixture to acid pH. Preferably, the hydrolysis-decarboxylation sequence can be conducted by heating to a temperature approximately ranging from 25° C. to the reflux temperature of the reaction mixture.

A thus prepared compound of formula (II), in which X is hydroxy, is in racemic form. If desired, a single enantiomer of a compound of formula (II) in which X is hydroxy, for example in the optically active (R) or (S) form, can be obtained by resolution of the racemic compound of formula (II), in which X is hydroxy, according to known methods. For example, said resolution can be carried out by crystallization of a diastereomeric salt obtained by treatment of a compound of formula (II), wherein X is hydroxy, with an optically active amine, such as (+) or (−) 1-phenylethylamine or (+) or (−) 1-naphthylethylamine or an alkaloid such as brucine, cinchonine or cinchonidine, according to the known procedure for the resolution via diastereomeric salts.

A compound of formula (II) in which X, being as defined above, is different from hydroxy, can be prepared starting from a compound of formula (II) wherein X is hydroxy, according to known methods.

For example, a compound of formula (II) wherein X is $C_1$-$C_4$ alkoxy can be obtained from a compound of formula (II) wherein X is hydroxy by esterification with a $C_1$-$C_4$ alkanol, according to known methods.

A compound of formula (II), as defined above in which X is $N_3$ as a single enantiomer or as a mixture thereof, can be obtained from a compound of formula (II) wherein X is hydroxy by treatment with diphenylphosphoryl azide (DPPA). Said compound of formula (II) can be isolated or used as such in the subsequent Curtius rearrangement.

It has herein unexpectedly been found an extremely advantageous procedure for carrying out the separation of the two optically active (R) and (S) forms from a racemic compound of formula (II).

According to a preferred aspect of the invention, a compound of formula (II) in the optically active (R) or (S) form, in which X is hydroxy, can be obtained by a process comprising the enantioselective enzymatic hydrolysis of one of the single (R) and (S) isomers of a racemic compound of formula (II), as defined above in which X is $C_1$-$C_4$ alkoxy, in the presence of an enzyme, in a solvent mixture.

In this way, one of the two enantiomeric alkyl esters of formula (II) which is not a substrate for the enzyme remains unchanged, while the other, being a substrate for the enzyme, is hydrolysed to obtain the corresponding carboxylic acid of formula (II), in the optically active (R) or (S) form.

An enzyme according to the invention is for example an enzyme belonging to the class of the hydrolases, and in particular to the lipase, protease and esterase subclasses. Preferably said enzyme is an enzyme active at a pH approximately between 5 and 9, preferably approximately between 6 and 8.5. Said enzyme can originate from various sources such as bacteria, fungi, animals or plants.

The enantiomer of formula (II) in optically active (R) form, in which X is hydroxy, can preferably be obtained by using a protease, in particular a protease obtained from a bacteria of the genus *Bacillus*, preferably *Bacillus licheniformis*, for example one of those named FE201® marketed by CLEA or one of those named Protex® produced by Genencor International, or one of those named Protin® provided by Amano.

A solvent mixture is for example formed by a solution comprising an aqueous buffer with pH approximately ranging between 5.0 and 9.0, more preferably approximately pH 8.0, and an organic cosolvent, which can be miscible or immiscible with the buffer.

A solution of an aqueous buffer can be selected for example from the group comprising a known buffer system, e.g. a phosphate, ammonium bicarbonate, ethanolamine/HCl, or borate buffer; the reaction is preferably carried out in phosphate buffer.

An organic cosolvent can be for example a solvent selected from the group comprising a polar aprotic solvent, typically dimethylformamide, dimethylacetamide, acetonitrile or dimethylsulfoxide; a ketone, typically acetone or methyl isobutyl ketone; an apolar aprotic solvent, typically toluene; and an ether, typically tetrahydrofuran or dioxane; preferably toluene.

The concentration of the racemic substrate of a compound of formula (II), in which X is $C_1$-$C_4$ alkoxy, in the solvent mixture, comprising a buffer solution and, if the case, an organic cosolvent, can approximately range from 0.1% to 50%, preferably approximately from 1% to 20%.

The reaction can be carried out at a temperature approximately ranging between 15 and 60° C., preferably approximately between 30 and 60° C., more preferably at about 50° C.

Reaction times depend on the reaction temperature and the enzyme used. Typically the enzyme is left to react until HPLC evidences an approximately 50% conversion of the starting racemate.

If the reaction is carried out in the presence of an automatic titrator, the reaction end point is set at, for example, at pH 8 and the solution is left under stirring until pH adjustments are no longer made by the titrator. According to the preferred conditions indicated above, the enzymatic hydrolysis is usually completed in approximately one day.

The compound of formula (II) in the optically active (S) form, in which X is $C_1$-$C_4$ alkoxy, which has not been hydrolysed by enzyme, can be isolated from the reaction mixture by extraction with a solvent, for example ethyl acetate. If desired, said compound of formula (II) in the optically active (S) form can be hydrolysed by saponification, as described above, to afford the compound of formula (II) in which X is hydroxy, which can be racemized according to known procedures and recycled in the process of the invention.

The enantiomer of formula (II) in the optically active (R) form, in which X is hydroxy, in the form of a salt of an alkali metal, preferably sodium, remains in the aqueous phase and can be recovered upon acidification and extraction with a solvent, for example with ethyl acetate.

Concentration of the organic solution provides the enantiomer of formula (II) in the optically active (R) form, in which X is hydroxy, in excellent yields, typically from about 40 to about 50% starting from the racemate of formula (II), in which X is $C_1$-$C_4$ alkoxy, and with chemical purity equal to or higher than 95%, preferably equal to or higher than 98%, as evaluated by HPLC.

The enantiomeric purity of the thus isolated optically active (R) enantiomer of formula (II), calculated by chiral HPLC, is expressed in terms of enantiomeric ratio and is typically equal to or higher than 96:4, preferably equal to or higher than 99:1.

The conversion according to the process of the invention of an optically active (R) compound of formula (II), having such unexpectedly high levels of chemical and enantiomeric purity, to a compound of formula (I) as defined above, affords said compound of formula (I) in extremely pure form from both the chemical and stereochemical point of view.

A compound of formula (V) can be prepared by alkylation of a compound of formula (VI)

wherein each $R_1$ is as defined above, with a compound of formula (VII) and (VIII)

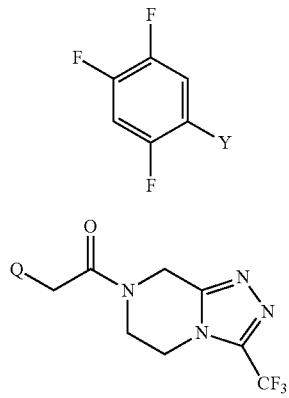
(VII)

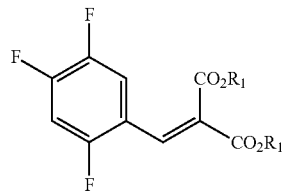
(XI)

wherein $R_1$ is as defined above, and alkylation of the compound of formula (IX) thus obtained with a compound of formula (VIII), as defined above.

The Knoevenagel reaction can be catalyzed in alkali or neutral medium by amines, for example piperidine or salts thereof. Alternatively, the Knoevenagel condensation can be carried out with a Lewis acid catalyst. A Lewis acid can be chosen from $ZnCl_2$, $FeCl_3$, $TiCl_4$, or Ti tetraisopropoxide, $AlCl_3$, or etherate $BF_3$, or a halide, for example a chloride, or a trifluoromethanesulfonate of a transition metal of the lanthanide series, preferably lanthanum trifluoromethanesulfonate in both the anhydrous and hydrated form.

The hydrogenation reaction can be carried out in an organic or aqueous solvent in the presence of a hydrogenation catalyst, preferably based on palladium or platinum, and in the presence of molecular hydrogen or of a reagent able of developing hydrogen in situ.

The compounds of formula (V) are novel and are a further object of the present invention.

The compounds of formula (VII) are commercially available or can be prepared with known procedures. The compounds of formula (VIII) can be prepared for example starting from the amine of formula (B), as shown in the scheme reported above, with known procedures, for example by using alkylating reagents, such as chloroacetyl chloride or bromoacetyl chloride.

The amine of formula (B) is commercially available or can be prepared according to known methods.

The following examples illustrate the invention.

(VIII)

wherein Y is a formyl group or a $CH_2Z$ group, wherein Z is a leaving group; and Q is a halogen, such as chlorine or bromine; and in the presence of a base.

A leaving group is for example mesylate, tosylate, p-nosylate, o-nosylate or a halogen, such as chlorine or bromine; preferably a halogen, more preferably chlorine or bromine.

A base can be for example a hydride, for example sodium hydride, or a $C_1$-$C_4$ alkoxide of an alkali metal, preferably sodium; or a tertiary amine, for example 1,8-diazabicyclo[5.4.0]undec-7-ene (DBU), 1,5-diazabicyclo-[4.3.0]non-5-ene (DBN), 1,4-diazabicyclo[2.2.2]octane (DABCO), lithiumdiisopropylamide (LDA), isopropyl-magnesium bromide or chloride, cyclohexyl-magnesium bromide or chloride, or a $C_4$-$C_6$ alkyl-lithium or phenyl-lithium. A compound of formula (VII) and a compound of formula (VIII) can be reacted singularly with a compound of formula (VI), isolating the respective monoalkylation intermediates of formula (IX) and (X),

Example 1

Synthesis of diethyl 2-(2,4,5-trifluorobenzylidene)-malonate of formula (XI, $R_1$=Et)

A solution obtained dissolving 2,4,5-trifluorobenzaldeide (4.0 g, 24.5 mmol) and diethyl malonate (4.0 ml, 25.8 mmol) in toluene (20 ml) is added, under stirring, with piperidine (200 ml, 2.0 mmol), benzoic acid (150 mg, 1.2 mmol) and $Na_2SO_4$ (6.0 g). The suspension is left under stirring at 110° C. for 10 h. After completion of the reaction, the suspension is cooled to room temperature, filtered and the filtrate is washed with 100 ml of water, 50 ml of 1N HCl, 50 ml of a $NaHCO_3$ saturated solution and finally with 50 ml of water (neutral pH). The organic phase is concentrated under reduced pressure to afford 8.5 g of crude product. The product is purified by flash chromatography (eluent: hexane/dichloromethane 6:4). The product (4.2 g, 13.9 mmol, 57% yield) is a yellow oil.

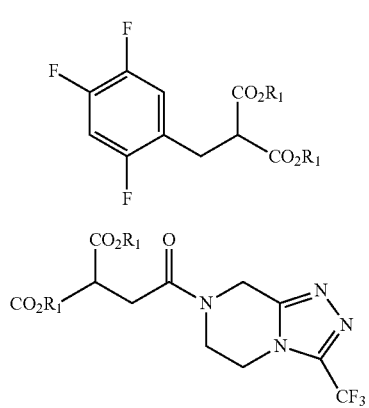

wherein $R_1$ is as defined above; or be added in sequence to isolate the only dialkylation product of formula (V).

Alternatively, the intermediate of formula (V) can be prepared by Knoevenagel condensation between a compound of formula (VII) wherein Y is a formyl group and a compound of formula (VI), as defined above, subsequent hydrogenation of the unsaturated intermediate of formula (XI)

$^1$H-NMR (300 MHz, $CDCl_3$): δ=7.75 (s, 1H), 7.38-7.28 (m, 1H), 7.02-6.92 (m, 1H), 4.35 (2×q, 4H), 1.30 (2×t, 6H).

Ms (EI)=302.

Example 2

Synthesis of diethyl 2-(2,4,5-trifluorobenzyl)malonate of formula (IX, $R_1$=Et)

A solution obtained dissolving diethyl 2-(2,4,5-trifluorobenzylidene)-malonate (3.1 g, 10.3 mmol) in ethanol (50 ml) is added, under stirring, with 5% Pd/C (2.4 g, 0.49 mmol). The suspension is heated to 80° C. and added in about 20 minutes with a solution obtained dissolving NaHCO$_2$ (2.1 g, 30.9 mmol) in water (15 ml). After completion of the addition, the mixture is left under stirring at 80° C. for 30 minutes. After completion of the reaction, the suspension is cooled to room temperature, and filtered through Celite washing the solids with methanol (50 ml). The filtrate is concentrated, added with 30 ml of ethyl acetate and the phases are separated. The organic phase is dried with Na$_2$SO$_4$ and filtered. The solvent is evaporated off under reduced pressure. The product (2.2 g, 7.2 mmol, 70% yield) is a yellow oil.

$^1$H-NMR (300 MHz, CDCl$_3$): δ=7.09-7.00 (m, 1H), 6.91-6.84 (m, 1H), 4.17 (q, 4H), 3.64 (t, 1H), 3.17 (d, 2H), 1.23 (t, 6H).

Ms (EI)=304.

Example 3

Synthesis 7-chloroacetyl-3-trifluoromethyl-5,6,7,8-tetrahydro-[1,2,4]triazolo[4,3-a]pyrazine of formula (VIII, Q=chlorine)

3-(Trifluoromethyl)-5,6,7,8-tetrahydro-[1,2,4]triazolo[4,3-a]pyrazine hydrochloride (1.0 g, 4.4 mmol) is suspended in toluene (10 ml) and added, under strong stirring, with water (1 ml) and a 30% NaOH solution (3 ml). After 10 minutes, the phases are separated, the aqueous phase is extracted with 3×10 ml of ethyl acetate and the organic phase is dried with Na$_2$SO$_4$, then filtered and the solvent is evaporated off under reduced pressure. The resulting product is dissolved in toluene (15 ml) at −10° C., added with triethylamine (750 ml, 5.4 mmol) then, under stirring and inert atmosphere, added in about 20 minutes with a solution obtained dissolving chloroacetyl chloride (400 ml, 4.9 mmol) in toluene (5 ml). The solution is left under stirring at a temperature ranging from 0° C. to −5° C. for 30 minutes. After completion of the reaction, 10 ml of water are added, the phases are separated and the aqueous phase is extracted with 3×10 ml of dichloromethane. The solvent is concentrated under reduced pressure, 20 ml of ethyl acetate are added, the organic phase is washed with 2 ml of water, the phases are separated and the aqueous phase is extracted with 10 ml of toluene. The solvent is concentrated under reduced pressure. The product (1.2 g, 4.3 mmol, 98% yield) is a yellow oil which can be crystallized from tetrahydrofuran/methyl tert-butyl ether.

$^1$H-NMR (300 MHz, CDCl$_3$): δ=5.04 (s, 2H), 4.36-3.98 (m, 4H), 4.18 (s, 2H).

Ms (EI)=268.

Example 4

Synthesis 7-chloroacetyl-3-trifluoromethyl-5,6,7,8-tetrahydro-[1,2,4]triazolo[4,3-a]pyrazine of formula (VIII, Q=chlorine)

3-(Trifluoromethyl)-5,6,7,8-tetrahydro-[1,2,4]triazolo[4,3-a]pyrazine hydrochloride (54.6 g, 239 mmol) is suspended in ethyl acetate (300 ml) and added, under strong stirring, with a 30% NaOH solution (100 g) and water (50 ml). After 10 minutes the phases are separated, the aqueous phase is extracted with 3×70 ml of ethyl acetate and the organic phase is dried with Na$_2$SO$_4$, then filtered and the solvent is evaporated off under reduced pressure to obtain a white solid (45.4 g, 236 mmol, 99% yield).

The resulting product is dissolved in tetrahydrofuran (200 ml) and the solution is added in about 90 minutes to a solution obtained dissolving chloroacetyl chloride (28.6 g, 253 mmol) in tetrahydrofuran (200 ml), under N$_2$ atmosphere and under stirring. The solution is left under stirring at 25° C. for 1 h. After completion of the reaction, a 25% NaOH solution (80 g) is added, the phases are separated and the aqueous phase is extracted with 2×100 ml of tetrahydrofuran. The solvent is concentrated under reduced pressure to obtain 160 g of a crude, which is added with methyl-tert-butyl ether (220 ml) and the solution is heated under reflux of the solvent mixture. The solution is cooled to 10° C. under strong stirring for 3 h. The product (56.1 g, 209 mmol, 89% yield) is a white solid.

Example 5

Synthesis of diethyl 2-[2-oxo-2-(3-trifluoromethyl-5,6-dihydro[1,2,4]triazolo[4,3-a]-7(8H)pyrazinyl) ethyl]-2-(2,4,5-trifluoro-benzyl)malonate of formula (V, $R_1$=Et)

A solution obtained dissolving diethyl 2-(2,4,5-trifluorobenzyl)-malonate (IX) (215 mg, 0.71 mmol) in tetrahydrofuran (5 ml), under N$_2$ atmosphere and under stirring, is added with 60% NaH (44 mg, 1.10 mmol) and a solution obtained dissolving 7-chloroacetyl-3-trifluoromethyl-5,6,7,8-tetrahydro-[1,2,4]triazolo[4,3-a]pyrazine, as prepared in Example 3, (200 mg, 0.74 mmol) in tetrahydrofuran (5 ml). The solution is left under stirring at 25° C. for 22 h. After completion of the reaction, 10 ml of water are added, the organic solvent is concentrated and 10 ml of ethyl acetate are added; the phases are separated, the aqueous phase is extracted with 2×10 ml of ethyl acetate and the organic phase is dried with Na$_2$SO$_4$, then filtered and the solvent is evaporated off under reduced pressure. The product is purified by flash chromatography (eluents: dichloromethane/methanol 97:3→dichloromethane/methanol/94:6). The product (220 mg, 0.41 mmol, 58% yield) is a pale yellow solid.

$^1$H-NMR (300 MHz, CDCl$_3$): δ=6.92-6.68 (m, 2H), 5.04 (bs, 1H), 4.88 (bs, 1H), 4.23 (q, 4H), 4.18-3.91 (bs, 4H), 3.52 (bs, 1H), 3.47 (bs, 1H), 2.94 (s, 2H), 1.27 (t, 6H).

Ms (ESI+)=538.16

Example 6

Synthesis of 4-oxo-2-(2,4,5-trifluorobenzyl)-4-(3-trifluoromethyl-5,6-dihydro[1,2,4]triazolo[4,3-a]-7(8H)-pyrazinyl)butyric acid of formula (II, X=hydroxy)

A solution obtained dissolving KOH (53 mg, 0.94 mmol) in water (2 ml) is added with a solution of diethyl 2-[2-oxo-2-(3-trifluoromethyl-5,6-dihydro-8H-[1,2,4]triazolo[4,3-a]pirazin-7-yl)ethyl]-2-(2,4,5-trifluorobenzyl)-malonate (200 mg, 0.37 mmol) in ethanol (7 ml). The resulting solution is heated at 80° C. for 5 h. Upon completion of the reaction, a 37% HCl solution is added to pH=2, the solvent is concentrated and the mixture diluted with ethyl acetate. The aqueous phase is extracted with 2×10 ml of ethyl acetate, the organic phase is dried with Na$_2$SO$_4$, filtered and the solvent is evaporated off under reduced pressure. The product is crystallized from a 10:3 MeOH/H₂O mixture (5 ml).

Ms (ESI+)=437.08.

Example 7

Synthesis of 4-oxo-2-(2,4,5-trifluorobenzyl)-4-(3-trifluoromethyl-5,6-dihydro[1,2,4]triazolo[4,3-a]-7(8H)-pyrazinyl)butyric acid of formula (II, X=hydroxy)

A solution obtained dissolving KOH (4.2 g, 74.6 mmol) in water (60 ml) is added with a solution of diethyl 2-[2-oxo-2-(3-trifluoromethyl-5,6-dihydro-8H-[1,2,4]triazolo[4,3-a]pirazin-7-yl)ethyl]-2-(2,4,5-trifluorobenzyl)-malonate (16 g, 30 mmol) in ethanol (160 ml). The resulting solution is heated at 80° C. for 10 h. Upon completion of the reaction, the solvent is concentrated and the aqueous phase is washed with 2×20 ml of ethyl acetate. The aqueous phase is added with a 37% HCl solution to pH=2, extracted with 3×50 ml of ethyl acetate, the organic phase is dried with Na₂SO₄, filtered and the solvent is evaporated off under reduced pressure. The product is crystallized from a H₂O/MeOH 80:20 solution.

Example 8

Resolution of 4-oxo-2-(2,4,5-trifluorobenzyl)-4-(3-trifluoromethyl-5,6-dihydro[1,2,4]triazolo[4,3-a]-7(8H)-pyrazinyl)butyric acid (to obtain II (R) or II (S), X=hydroxy)

A solution obtained dissolving 4-oxo-2-(2,4,5-trifluorobenzyl)-4-(3-trifluoromethyl-5,6-dihydro[1,2,4]triazolo[4,3-a]-7(8H)pyrazinyl)butyric acid in ethanol is added with (S)-(−)-FEA or (R)-(+)-FEA. The mixture is heated to obtain a clear solution, then the solution is cooled to room temperature. The crystalline solid is filtered, washed with cold ethanol and dried. The resulting salt is dissolved in water, added with a 37% HCl solution to pH=1 and the aqueous solution is extracted with dichloromethane and ethyl acetate. The organic phase is dried with Na₂SO₄, filtered and the solvent is evaporated off under reduced pressure to afford the optically active product of formula (II) in which X is hydroxy, of (R) or (S) configuration.

Example 9

Resolution of 4-oxo-2-(2,4,5-trifluorobenzyl)-4-(3-trifluoromethyl-5,6-dihydro[1,2,4]triazolo[4,3-a]-7(8H)-pyrazinyl)butyric acid (II) with (L)-cinchonidine A solution obtained dissolving 4-oxo-2-(2,4,5-trifluorobenzyl)-4-(3-trifluoromethyl-5,6-dihydro[1,2,4]triazolo[4,3-a]-7(8H)pyrazinyl)butyric acid (7.2 g, 16.5 mmol) in tetrahydrofuran (35 ml) is added with cinchonidine (5.1 g, 16.5 mmol) and left under stirring. After 20 minutes a white solid precipitates, diluted with tetrahydrofuran (15 ml), the solid is filtered and dried at 30° C. under reduced pressure for 3 h. The product (6.3 g, 8.2 mmol) is dissolved in AcOEt (40 ml) and the organic solution is washed with 1N HCl solution (3×10 ml). The phases are separated, the organic phase is dried with Na₂SO₄, filtered and the solvent is evaporated off under reduced pressure. The acid is recovered as a white solid (3.6 g, 8.2 mmol) and consists of two enantiomers in 82:18 (II)(S):(II)(R) ratio, as evaluated by chiral HPLC.

Example 10

Synthesis of methyl 4-oxo-2-(2,4,5-trifluorobenzyl)-4-(3-trifluoromethyl-5,6-dihydro[1,2,4]triazolo[4,3-a]-7(8H)-pyrazinyl)-butyrate (II, X=methoxy)

A solution obtained dissolving 4-oxo-2-(2,4,5-trifluorobenzyl)-4-(3-trifluoromethyl-5,6-dihydro[1,2,4]triazolo[4,3-a]-7(8H)-pyrazinyl)butyric acid (1.0 g, 2.3 mmol) in methanol (5 ml) is added with 95% H₂SO₄ (200 µl) and left under stirring at 25° C. for 16 h. After completion of the reaction, the mixture is neutralized with a NaHCO₃ saturated solution, concentrated under reduced pressure and the residue is diluted with AcOEt (15 ml). The phases are separated, the organic phase is dried with Na₂SO₄, filtered and the solvent is evaporated off under reduced pressure. The product is purified by flash chromatography (eluents: AcOEt/hexane 8:2→AcOEt/hexane 9:1). The product (1.0 g, 2.1 mmol, 95% yield) is a white solid.

¹H-NMR (300 MHz, CDCl₃): δ=7.06-6.94 (m, 2H), 4.92 (bs, 2H), 4.30-3.90 (m, 4H), 3.68 (s, 3H), 3.27 (bs, 1H), 278-2.04 (m, 3H), 2.48-2.38 (dd, 1H).

Example 11

Enzymatic hydrolysis of methyl 4-oxo-2-(2,4,5-trifluorobenzyl)-4-(3-trifluoromethyl-5,6-dihydro[1,2,4]triazolo[4,3-a]-7(8H)-pyrazinyl)butyrate (II, X=methoxy)

A solution obtained dissolving methyl 4-oxo-2-(2,4,5-trifluorobenzyl)-4-(3-trifluoromethyl-5,6-dihydro[1,2,4]triazolo[4,3-a]-7(8H)-pyrazinyl)-butyrate as prepared in Example 10 (14.7 g, 32.6 mmol) in toluene (147 ml) is added with a solution of 0.125 M phosphate buffer (295 ml) at pH=8.1, H₂O (146 ml) and a solution of protease from *Bacillus licheniformis* (295 ml). The mixture is left under strong stirring at 50° C. for 6 h, regularly adjusting pH with a 10% NaOH solution to maintain it in a range between 7 and 8.5. After completion of the reaction, the reaction mixture is filtered through Celite, the phases are separated and the aqueous phase is washed with toluene (350 ml). The aqueous phase is added with 37% HCl (25 ml) to pH=1. The solution is again filtered through Celite and diluted with ethyl acetate (1×1). The phases are separated, the organic phase is dried with Na₂SO₄, filtered and the solvent is evaporated off under reduced pressure. The acid with configuration (R) is collected as a brown oil (4.6 g, 10.5 mmol) and has optical purity higher than 99.9%, evaluated by chiral HPLC.

Example 12

Synthesis of 2-(R)-4-oxo-4-[3-(trifluoromethyl)-5,6-dihydro[1,2,4]triazolo[4,3-a]-7(8H)-pyrazinyl]-1-(2,4,5-trifluorophenyl)-2-butanamine dodecylthio carbamate (IV, R=dodecylthio)

A solution obtained dissolving 2-(R)-4-oxo-2-(2,4,5-trifluorobenzyl)-4-(3-trifluoromethyl-5,6-dihydro[1,2,4]triazolo[4,3-a]-7(8H)pyrazinyl)butyric acid II-(R) (4.6 g, 10.5 mmol)—obtained in Example 11—in tetrahydrofuran (35 ml) is added with triethylamine (2.1 ml, 15 mmol) and a solution obtained dissolving DPPA (3.5 g, 12.7 mmol) in tetrahydrofuran (20 ml). The reaction mixture is left under stirring and inert atmosphere for 1 h at about 25° C., then is slowly added dropwise (about 1 h) with a solution obtained dissolving 1-dodecanethiol (7.6 ml, 31.7 mmol) in tetrahydrofuran (15 ml) a 65° C. After completion of the addition, the resulting reaction mixture is left under stirring for 90 min at 65° C. The solvent is concentrated under reduced pressure and the reaction crude is diluted in AcOEt (70 ml); the organic solution is washed with $H_2O$ (50 ml), the phases are separated and the organic solution is partially concentrated under reduced pressure. The mixture is further diluted by addition of hexane (50 ml), to obtain a white solid which is filtered and washed with hexane. The product (5.2 g, 8.2 mmol) is dried at 30° C. under reduced pressure for 3 h to afford a 78% yield. Ms (ESI+)=636.99.

Example 13

Synthesis of 2-(R)-4-oxo-4-[3-(trifluoromethyl)-5,6-dihydro[1,2,4]triazolo[4,3-a]-7(8H)-pyrazinyl]-1-(2,4,5-trifluorophenyl)-2-butanamine (I with configuration R), i.e. Sitagliptin A solution obtained dissolving 2(R)-4-oxo-4-[3-(trifluoromethyl)-5,6-dihydro[1,2,4]triazolo[4,3-a]-7(8H)-pyrazinyl]-1-(2,4,5-trifluorophenyl)-2-butanamine dodecylthio carbamate IV-(R) (5.2 g, 8.2 mmol) in isopropanol (30 ml) is added with a solution obtained dissolving NaOH (1.1 g, 24.5 mmol) in $H_2O$ (50 ml). The solution is left under stirring a 50° C. for 1.5 h. Upon completion of the reaction, the organic solvent is concentrated and the aqueous phase is extracted with 3×40 ml of AcOEt. The phases are separated, the organic phase is dried with $Na_2SO_4$, filtered and the solvent is evaporated off under reduced pressure, to afford a pale yellow solid. Ms (ESI+)=407.97.

The invention claimed is:

1. A process for the preparation of a compound of formula (I), or a pharmaceutically acceptable salt, racemate, enantiomer or optically active mixture thereof,

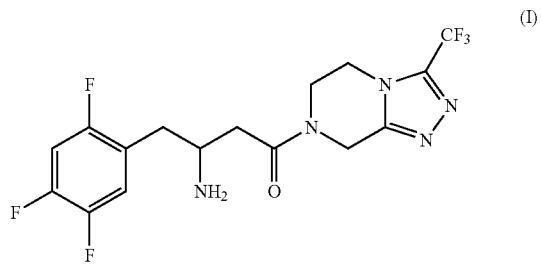

comprising the conversion of a compound of formula (II), or a pharmaceutically acceptable salt, racemate, enantiomer or optically active mixture thereof,

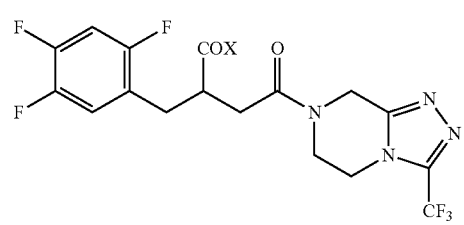

wherein X is selected from the group consisting of hydrogen, hydroxy, $C_1$-$C_8$ alkyl, $C_1$-$C_4$ alkoxy, aryl, amino, $N_3$ and halogen; into a compound of formula (I) or a pharmaceutically acceptable salt, racemate, enantiomer or optically active mixture thereof.

2. A process according to claim 1, wherein a compound of formula (II), or a racemate, enantiomer or optically active mixture thereof, wherein X is $N_3$, is converted via Curtius rearrangement into an intermediate isocyanate of formula (III), or a racemate, enantiomer or optically active mixture thereof;

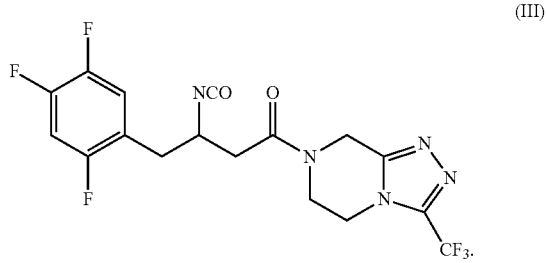

3. A process according to claim 2, comprising the conversion of a compound of formula (II), wherein X is hydroxy, into a compound of formula (II) wherein X is $N_3$, by treatment with diphenylphosphoryl azide, and subsequent conversion of the compound of formula (II) via Curtius rearrangement into a compound of formula (I).

4. The process according to claim 2, further comprising: (a) resolving an enantiomer of formula (I) from a racemate or optically active mixture thereof, (b) converting a compound of formula (I) into a pharmaceutically acceptable salt thereof; and/or (c) converting a pharmaceutically acceptable salt of formula (I) into a compound of formula (I).

5. A process according to claim 1, wherein a compound of formula (II), or a racemate, enantiomer or optically active mixture thereof, wherein X is $N_3$, is converted via Curtius rearrangement in the presence of a $C_1$-$C_4$ alkanol, $C_2$-$C_{20}$ alkylthiol, arylthiol, or aryl-$C_1$-$C_4$-alkylthiol, into a compound of formula (IV) or a racemate, or an enantiomer or optically active mixture thereof

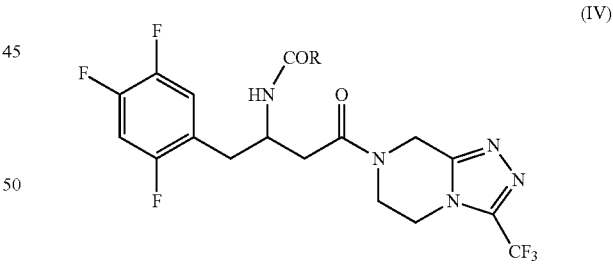

wherein R is a $C_1$-$C_4$ alkoxy, $C_2$-$C_{20}$ alkylthio, arylthio, or aryl-$C_1$-$C_4$ alkylthio group.

6. A process according to claim 5, wherein the $C_1$-$C_4$ alkanol is selected from isopropanol and tert-butanol and the $C_2$-$C_{20}$ alkylthiol is dodecanethiol.

7. The process according to claim 5, further comprising: (a) resolving an enantiomer of formula (I) from a racemate or optically active mixture thereof, (b), converting a compound of formula (I) into a pharmaceutically acceptable salt thereof; and/or (c) converting a pharmaceutically acceptable salt of formula (I) into a compound of formula (I).

8. A process according to claim 1, further comprising the preparation of an enantiomer of the compound of formula (II), wherein X is hydroxy, comprising the enantioselective enzymatic hydrolysis of one of the enantiomers of a racemate of formula (II), wherein X is $C_1$-$C_4$ alkoxy, in the presence of a hydrolase, in a solvent mixture.

9. A process according to claim 8, wherein the hydrolase is selected from the group consisting of a lipase, a protease and an esterase.

10. A process according to claim 9, wherein the enantiomer of formula (II) is the (R)-enantiomer of formula (II) and said is a *Bacillus* genus protease.

11. A process according to claim 1, wherein a compound of formula (II), or a racemate, enantiomer or optically active mixture thereof, wherein X is $NH_2$, is converted via Hofmann degradation into a compound of formula (I) or a racemate, enantiomer or optically active mixture thereof.

12. The process according to claim 11, further comprising: (a) resolving an enantiomer of formula (I) from a racemate or any optically active mixture thereof; (b) converting a compound of formula (I) into a pharmaceutically acceptable salt thereof; and/or (c) converting any pharmaceutically acceptable salt of formula (I) into a compound of formula (I).

13. A process according to claim 1, wherein a compound of formula (II), or a racemate, enantiomer or optically active mixture thereof, wherein X is hydroxy, is converted via the Lossen or Schmidt procedure into a compound of formula (I) or a racemate, enantiomer or optically active mixture thereof; via formation of an intermediate isocyanate of formula (III),

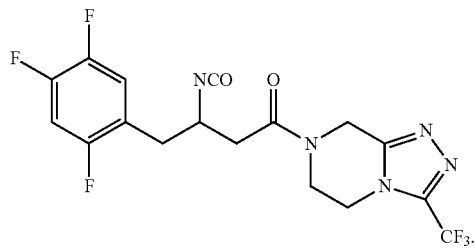

(III)

14. A process according to claim 1, further comprising the preparation of a compound of formula (II), wherein X is hydroxy, comprising the hydrolysis and the decarboxylation of a compound of formula (V)

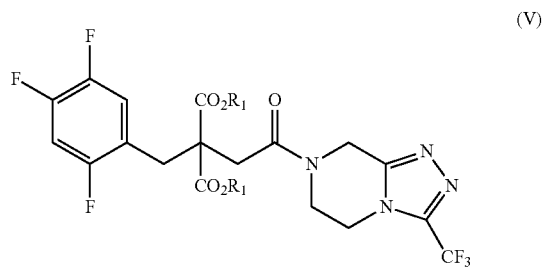

(V)

wherein each $R_1$, independently is straight or branched $C_1$-$C_4$ alkyl, to obtain a compound of formula (II).

15. A process according to claim 1, further comprising the preparation of an enantiomer of the compound of formula (II) wherein X is hydroxy, by a resolution process comprising crystallization of a pharmaceutically acceptable diastereomeric salt of the compound of formula (II).

16. The process according to claim 1, further comprising: (a) resolving an enantiomer of formula (I) from a racemate or optically active mixture thereof, (b) converting a compound of formula (I) into a pharmaceutically acceptable salt thereof, and/or (c) converting a pharmaceutically acceptable salt of formula (I) into a compound of formula (I).

* * * * *